United States Patent [19]

Harris et al.

[11] Patent Number: 4,614,428
[45] Date of Patent: Sep. 30, 1986

[54] HIGH-TEMPERATURE, HIGH-PRESSURE OPTICAL CELL

[75] Inventors: Ronald P. Harris, Decatur; Lawrence R. Holland, Huntsville, both of Ala.; Robbie E. Smith, Fayetteville, Tenn.

[73] Assignee: The United States of America as represented by the Administrator of the National Aeronautics and Space Administration, Washington, D.C.

[21] Appl. No.: 571,615

[22] Filed: Jan. 17, 1984

[51] Int. Cl.⁴ .................................... G01N 21/03
[52] U.S. Cl. .................................... 356/246; 372/61
[58] Field of Search ................ 372/34, 33, 55, 61, 372/92; 356/246

[56] References Cited

U.S. PATENT DOCUMENTS 3,583,817  6/1971  Rachlis et al. ............... 356/246 X
3,740,158  6/1973  Bellinger et al. ............. 356/246

OTHER PUBLICATIONS

Noble et al, "All Quartz Optical Cell of Constant Diameter for Use in High Pressure Studies", Rev. Sci. Instrum., vol. 47, No. 6, Jun. 1976, pp. 770-771.

Primary Examiner—Vincent P. McGraw
Attorney, Agent, or Firm—Joseph H. Beumer; John R. Manning; Leon D. Wofford, Jr.

[57] ABSTRACT

The invention is an optical cell for containment of chemicals under conditions of high temperature and high pressure and a method of making the optical cell. As shown in FIG. 1, the cell (10) is formed of a vitreous silica tube (14), two optical windows (16) comprising vitreous silica rod inserted into the ends of tube (14) and fused into position in the tube ends. Windows (16) are spaced apart to form a cavity (18) enclosed by the tube (14) and the windows (16). A hole (20) is drilled radially through the tube (14) and into the cavity (18). Another vitreous silica tube is fused to silica tube (14) around the hole (20) to form stem (22), which is perpendicular to the long axis of tube (14). The open end of stem (22) is used to load chemicals (12) into cavity (18). Then stem (22) may be sealed and, if desired, it may be shortened in order to reduce the volume of cavity (18), which extends into stem (22).

8 Claims, 10 Drawing Figures

HIGH-TEMPERATURE, HIGH-PRESSURE OPTICAL CELL

ORIGIN OF THE INVENTION

The invention described herein was made in the performance of work under a NASA contract and is subject to the provisions of Public Law 96-517 (94 Stat. 3019; 35 USC 200-211).

TECHNICAL FIELD

The present invention relates generally to optical cells and more particularly to sealed optical cells capable of holding chemical melts under conditions of high temperature and high internal pressure.

BACKGROUND OF THE INVENTION

In the course of conducting space activities involving the growing of crystals under zero gravity conditions, the National Aeronautics and Space Administration first had a need to measure the thermal diffusivity of mercury-cadmium telluride (HgCdTe) melts by the infrared laser pulse method. However, such measurements of materials with high vapor pressure have not been commonplace in the past. In the past, diffusivity measurements worked with materials of low vapor pressure only. Therefore, because of the high vapor pressure of mercury, prior diffusivity measurement techniques were not applicable to mercury-cadmium telluride. To develop such techniques for mercury-cadmium telluride, optical cells capable of withstanding internal pressures of about 100 atmospheres at temperatures up to about 1000° C. were required to perform the necessary tests. In addition, the cells had to be transparent and capable of passing light without distortion, so that the chemical in the cell could be pulsed by a laser, observed under a microscope or that high quality photographs could be made. However, it was found that optical cells capable of passing light without distortion and also capable of handling such high temperatures and pressures are not known in the prior art and therefore are not available on the commercial market.

What is state-of-the-art and also available on the commercial market is a type of optical cell having windows made as thin lids fused over the ends of the cylindrical center portion. The windows on this type of cell are deliberately made thin so as to avoid distortion when they are fused to the body. Therefore, this type cell does not have the structural strength needed to handle high pressures.

Therefore, the object of this invention is to provide an optical cell with flat faces to hold mercury-cadmium telluride melts for the measurement of the thermal diffusivity by the infrared laser pulse technique. Another object is that the optical cell have the following features: (1) must be infrared transparent, (2) must withstand internal pressures of the order of 100 atmospheres at temperatures up to 1000° C., (3) must not react chemically with mercury, cadmium, tellurium, or the probable impurities of these elements, (4) must be hermetically sealed, and (5) must not have voids or vapor spaces in the optical cavity when filled.

SUMMARY OF THE INVENTION

The present invention is an optical cell for containment of chemicals under conditions of high temperature and high pressure and a method of making the optical cell. The optical cell comprises: a tube; two optical windows fused into opposite ends of said tube, said optical windows being spaced apart to form a cavity inside the center portion of said tube; a hole drilled radially through said tube into said cavity; and a hollow stem fused to said tube around said hole for loading said cavity, whereby said stem may be sealed after said cavity is loaded.

The method of making the optical cell for the containment of chemicals under conditions of high temperature and high internal pressure comprises the steps of: polishing one end of each of a plurality of short lengths of vitreous silica (also commonly called "fused quartz") rod, to be used as plugs; inserting the polished ends of said short lengths of vitreous silica rod as plugs into both ends of a vitreous silica tube, the tube having an inside diameter just large enough to accommodate the outside diameter of said short lengths of vitreous silica rod; fusing one end of a silica rod handle to the outside, unpolished end of each of said silica rod plugs; spacing the polished ends of said silica rod plugs apart to form a cavity enclosed by said tube and said plugs; fusing the opposite ends of said handles to the inside wall of said tube so as to hold said plugs in fixed position; fusing said plugs in position under vacuum; sawing off both ends of the tube at the point where the handles are attached to said plugs; annealing the cell formed by the tube and the plugs; drilling a hole through the tube radially into the cell cavity; fusing a tubular stem over the hole so that the stem is perpendicular to the tube; annealing the cell a second time to remove stress in the cell developed by attaching the stem; sawing off both cell ends closer to the cavity; and polishing both said cell ends.

BRIEF DESCRIPTION OF THE DRAWINGS

A presently preferred embodiment of the invention will now be described in detail in connection with the accompanying drawings wherein.

Detailed Description of the Invention

Figure 1:
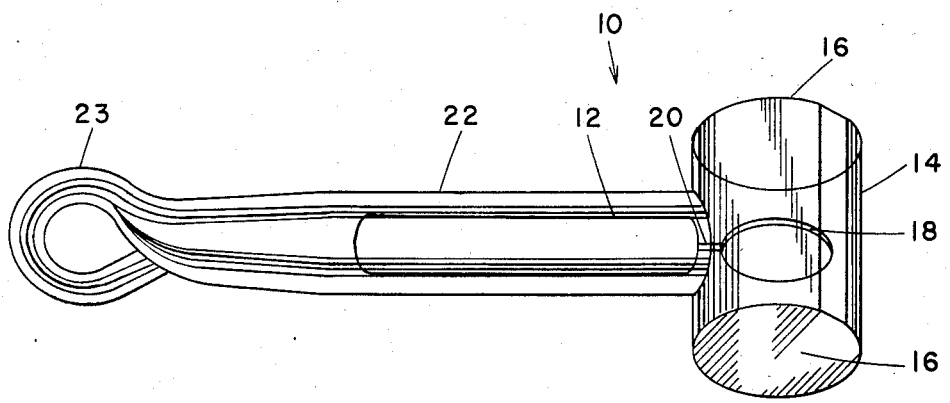
FIG. 1 shows a side view of the optical cell, including the long stem and the ring used to suspend the cell in a furnace.

FIG. 1 shows a side view of a finished optical cell 10, already loaded with a chemical 12 and hermetically sealed. The cell is formed of a vitreous silica tube 14, two optical windows 16 comprising vitreous silica rod inserted into the ends of tube 14 as plugs and fused into position in the tube ends. Using this mode of construction, windows 16 may be made arbitrarily thick to withstand high pressure. Also, the joints between the windows 16 and tube 14 are strong, since they operate in shear rather than in tension, as do the known prior art devices. Window distortion is avoided during fusion by heating the wall of tube 14 rather than the windows 16. The windows 16 are spaced apart to form a cavity 18 enclosed by the tube 14 and the windows 16. A hole 20 is drilled radially through the tube 14 and into the cavity 18. Another vitreous silica tube is fused to silica tube 14 around the hole 20 to form stem 22, which is perpendicular to the long axis of tube 14. The open end of stem 22 is used to load chemicals into cavity 18. Then stem 22 may be sealed and a loop 23 may be formed in the end of stem 22 for hanging the cell 10 in a furnace. Later, stem 22 may be shortened in order to reduce the volume of cavity 18, which extends into stem 22. Thus, as may be seen in FIG. 1, the cell 10 provides a distortion-free optical path through both windows 16 in order to pass light through the cell 10 or to view the chemical 12 in the cavity 18 under various conditions of high temperature and high pressure. This requires that the outside of each window has been polished also, as will be explained below.

Figures 2A, 2B:
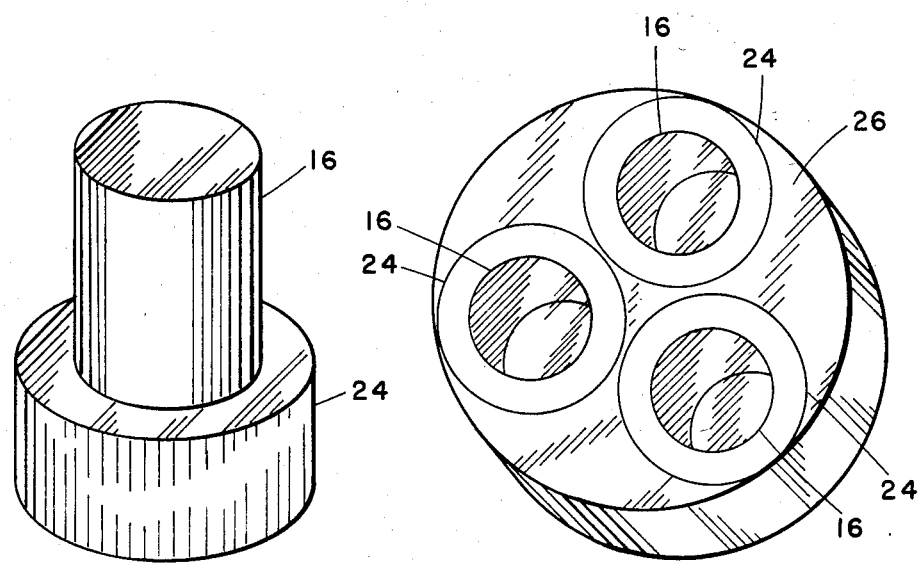
FIG. 2a is a perspective view of a window mounted in a guard ring.
FIG. 2b is a perspective view of three windows mounted in guard rings and embedded in epoxy for polishing.
Figure 3A:
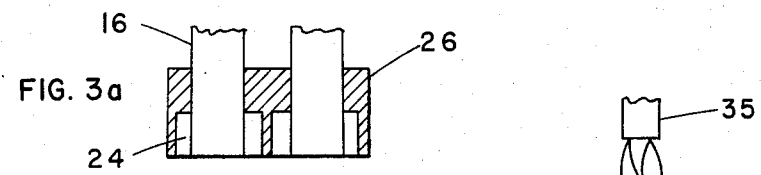
FIG. 3a shows a schematic sectional view of two windows mounted in epoxy for polishing.

To construct the cell 10, the first and most timeconsuming part of the process is polishing the windows 16. The windows 16 are made from 10 mm diameter vitreous silica rod, initially sawed into 25 mm lengths which should be inspected for striae and bubbles. These are inserted into 7 mm lengths of 10 mm i.d., 16 mm o.d. silica tube which serve as guard rings 24 during grinding and polishing (see FIG. 2a). Guard rings 24 are needed lest the windows 16 become convex or develop rounded edges, and should be selected to fit as closely as possible. Sets of three guard rings 24 with their windows 16 are cast into a commercially available epoxy, Fulton "Quickmount," in a 35 mm diameter mold (not shown), making an epoxy cast 26, as shown in FIG. 2b. A sectional view of two windows 16 mounted in epoxy casting 26 for polishing is shown in FIG. 3a. This assembly is then hand ground flat with 240 to 600 grit abrasive paper, and finally ground and polished on a Buehler "Minimet 1000" polisher, using 600 grit paper, 6 micron diamond, and finally 1 micron diamond abrasive. Vitreous silica is easy to scratch and hard to polish, so whenever two of the three windows 16 are ready for the next stage, the grit is changed and the third window 16 is carried along simply to stabilize the system mechanically. These "third windows" 16 are set aside and saved until a full set of three has accumulated, when they are cycled back into the process. Only one end of each window 16 is polished at this stage.

Figure 3B:
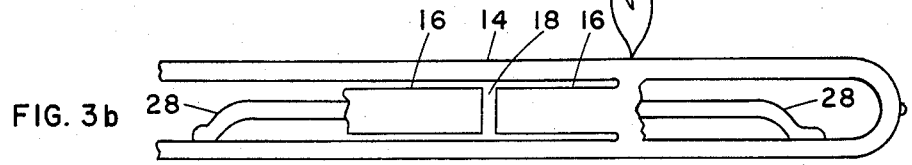
FIG. 3b is a schematic sectional view showing the first window being fused into a tube to form the optical cell.
Figure 3C:
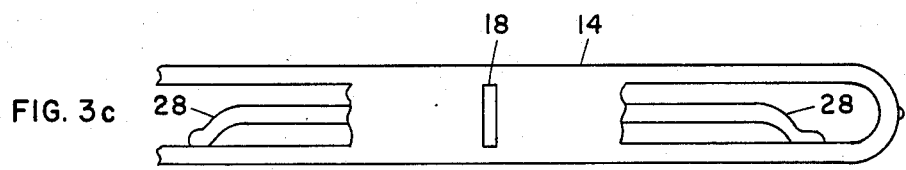
FIG. 3c is a schematic sectional view showing both windows completely fused into a tube to form the optical cell.
Figure 3D:
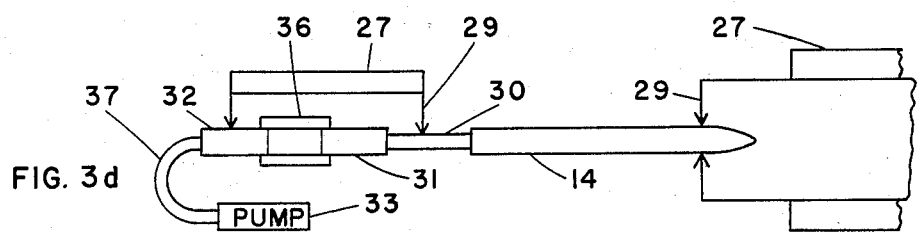
FIG. 3d is a schematic sectional view showing how the tube is mounted in a glassblower's lathe while the cell is being formed.

Looking now at FIG. 3b, the assembly of cell 10 is started by fusing two of the windows 16, polished ends inward and, in this embodiment, separated by 1 or 2 mm, into a 10 mm i.d., 16 mm o.s. silica tube 14, about 15 cm long. For this procedure each window 16 is provided with a "handle" 28, made by fusing a 4 mm diameter rod to the unpolished end. The back end of each handle 28 is tacked (fused) to the inside of the tube 14 so as to fix the position of the windows 16. The tube 14 is then placed in a glassblowing lathe 27, one end closed, and the other end attached through a graded seal 30, pyrex section 31 and a swivel 32 to a vacuum pump 33 (FIG. 3d). The windows 16 are fused to the tube 14 under vacuum, using an oxy-hydrogen torch 35 and working toward the vacuum pump 33 so as not to trap bubbles. Care must be taken in this step, as the working temperature range of vitreous silica is small, and the cell 10 will deform or collapse if the silica is slightly overheated. (See FIG. 3b, 3c, and 3d.) As is understood by those familiar with the glassblowing art, it is necessary to insert heat insulating means, namely, the graded seal 30 and the pyrex section 31, between the silica tube 14 and the glassblower's swivel 32, in order to protect swivel 32 and hoses 36 and 37 from heat radiation. As may be seen in FIG. 3e, both ends of the tube 14 are now sawed off where the handles 28 attach to the windows 16. The tube 14 and window 16 assembly is then annealed, following the NBS (National Bureau of Standards) recommended schedule: the temperature is raised at a constant rate to 1145° C. in four hours, held at 1145° C. for 20 min., cooled to 900° C. at 2° C./min., and then cooled to 500° C. at not more than 5° C./min. Cleanliness is critical, as contamination causes devitrification of vitreous silica.

Figure 3E:
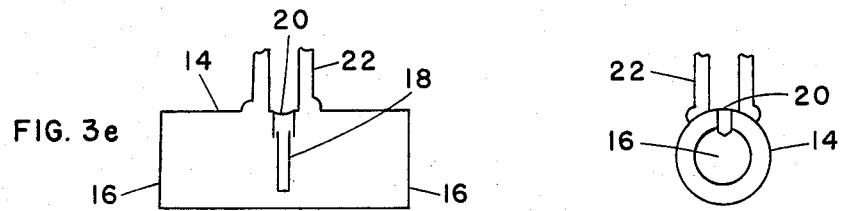
FIG. 3e is a schematic diagram showing both side and end views of the nearly completed cell with the tube ends cut off and the stem attached.
Figure 3F:
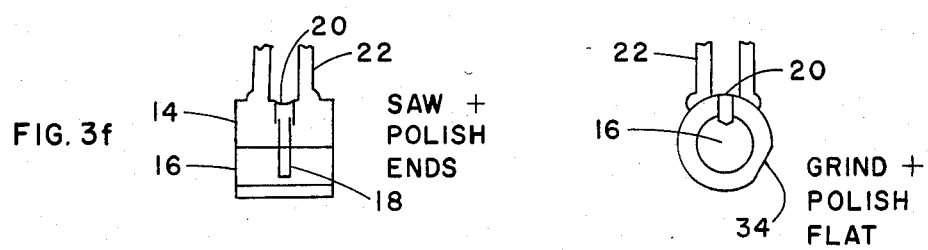
FIG. 3f is a schematic diagram showing both side and end views of the completed cell with a flat surface polished on the side.

A 2 mm diameter hole 20 is drilled radially into the cell cavity 18 with a diamond drill. Any attempt to do this before annealing leads to instant shattering. After drilling, a side arm or "stem" 22, is fused to the cell 10 over the hole 20. The stem 22 is made from 5 mm i.d., 10 mm o.d. clear silica tube, 15 cm long. This is a hand operation which leaves severe strains in the cell 10, and so the next step, cutting off the excess 16 mm tube at each end of the cell 10, must not be done too close. It has been possible to saw the cell 10 to a length of 40 mm with a diamond saw. This stage is shown in FIG. 3e. A second NBS anneal is used to remove the strains left by the stem attachment procedure; the cell 10 is sawed off to its final length of 18 mm, and the ends are ground and polished by hand. A grinding jig helps to maintain flatness. In order to make the critical measurement of the internal cell thickness, a flat surface 34 is ground and polished on one side of the cell 10. Through this flat surface 34, the edge of the cell cavity 18 can be observed with a microscope (not shown) equipped with a micrometer driven stage, and the internal cell thickness determined. FIG. 3f shows the final form of the cell 10.

Figure 4:
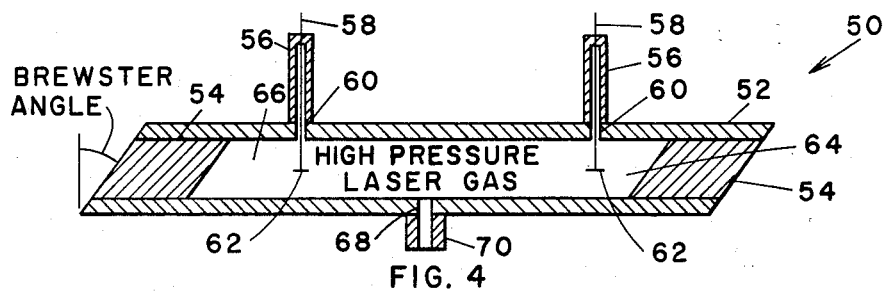
FIG. 4 shows an alternative embodiment of the invention wherein the invention is a high pressure discharge tube in a high pressure gas laser.

FIG. 4 shows another embodiment of the invention. Here, the invention is being used as a high pressure discharge tube 50 in a high pressure gas laser. In this embodiment, vitreous silica tube 52 has two windows 54 fused into the ends of the tube 52. A plurality of stems 56 are fused to one side of tube 52 in order to accommodate D.C. power leads 58. The leads 58 enter tube 52 through drilled holes 60 and carry power to electrodes 62, which excite laser gas 64 contained in cavity 66. An additional hole 68 is drilled in tube 52 and an additional stem 70 is fused to tube 52 in the manner already described for the cell shown in FIG. 3e above. Stem 70 is used for loading the gas into cavity 66. Windows 54 are cut and polished inside and outside to the Brewster angle, an arrangement to reduce reflection losses, which is known and understood by persons skilled in the art of optics (See *Optics,* Eugene Hecht and Alfred Zajac, Addison esley Publishers, 1974, pp. 485 and 486; and *Lasers in Industry,* S. S. Charschan, Van Nostrand Rheinhold, 1972, p. 618). The surfaces of windows 54 also may be coated to serve as laser cavity mirrors. High pressure gas laser tubes also may be excited by flashlamps or radio frequency discharge, in which cases the electric feedthroughs are not needed.

When first practicing the making of the cells, it has been found advisable to make a few trial assemblies with windows 16 which are only roughly polished, since the use of finished windows 16 during the learning phases is unnecessarily time-consuming. As the technique of making the cells is mastered, then the step of polishing the windows at the proper time may be added.

The cells 10 disclosed herein have been loaded with various compositions of mercury-cadmium telluride (HgCdTe) and have been used for the measurement of thermal diffusivity with great success. In such a usage, they are loaded with the purified elements and the alloy is synthesized in situ. The largest practical pieces of cadmium and tellurium are weighed and placed in the stem 22, after which the preweighed mercury is tipped in under vacuum. Sorption pumps work well, since they are fast and maintain a very low water vapor pressure. The stem 22 is sealed without breaking the vacuum, and a ring 23 is formed adjacent to the seal. The loaded cell 10, suspended by its ring 23 and with a tight wrapping of "Fiberfrax" or "Aten" ceramic fiber insulation (not shown) on the stem 22, is placed in a rocking furnace (not shown) to react the elements and homogenize the charge 12. The rocking position must be limited between ring downward and horizontal so that unhomogenized material does not enter the cavity 18. Once homogenization is compete, the furnace is tipped up and the HgCdTe cast into the cavity 18, which is then lowered out of the furnace so that only the very end shows. A compressed air jet directed at the bottom of the cell 10 quenches the charge, while the insulation wrapped on the stem assures a directional freeze from the bottom up. In this way expansion cracking is avoided. It is always essential to refreeze the charge directionally, or cracks will appear at the edge of the cell cavity 18, making the cell too weak to be reheated.

Once the charge 12 is cast, the stem may be shortened to limit the vapor space, as described above. This loading procedure preferably also should be used with other semiconductor materials which expand on freezing. In one series of measurements, eight out of eight cells 10 were loaded without mishap, and used at temperatures up to 900° C. and internal pressures up to 75 atmospheres. Although the bursting strength of these cells has not been tested, it is believed to be much higher than 75 atmospheres, perhaps as high as 200 atmospheres at 1150° C.

The preferred embodiment of the invention which has been disclosed herein has a short optical path, because that arrangement was best for the particular use for which the cell was developed, namely, measuring the diffusivity of mercury-cadmium telluride. However, it should be understood that the invention is also useful for many other laboratory purposes and for the containment of many other chemical compounds under conditions where an optical cell is needed and high temperatures and high pressures will occur. For example, the cell can be used for the observation of meniscus behavior near the critical points of many different high vapor pressure materials. Moreover, the invention may be embodied as a long path cell, i.e., when the cavity is long compared to the diameter. One example of this, when the invention is embodied as a high pressure laser gas cell, has already been described above and shown in FIG. 4.

It should be understood that, although vitreous silica ("fused quartz") has been described as a preferred material for making the invention, other vitreous materials may also be used. Alumina may be used for higher temperatures, pyrex glass may be used for economy at lower temperatures, and where infrared light transmission is not required, lead glass and the like may be used.

It also will be understood that the invention may be embodied in other specific forms without departing from the spirit or central characteristics thereof. The present examples and embodiments, therefore, are to be considered in all respects as illustrative and not restrictive, and the invention is not to be limited to the details given herein but may be modified within the scope of the appended claims.

We claim:

1. An optical cell for containment of chemicals under conditions of high temperature and high internal pressure comprising:
    a cell body comprising a tube;
    two optically-polished windows made of material identical to the material of which said tube is made, said windows being inserted into and fused into opposite ends of said tube, said optical windows being precisely spaced apart to form a cavity of arbitrary convenient length, thereby determining a desired precise cavity volume inside the center portion of said tube;
    said windows each being thicker than the thickness of said cavity, for providing a cell capable of containing high internal pressure without outside support;
    at least one hole extending radially through said tube into said cavity;
    at least one hollow stem made of material identical to said material of which said tube and said windows are made, said stem being fused to said tube around said hole for loading said cavity;
    whereby said stem may be sealed by fusing after said cavity is loaded.

2. The optical cell of claim 1 wherein said tube, said windows, and said stem are all made of transparent vitreous silica in order for said cell to be able to withstand very high temperatures.

3. The optical cell of claim 1 wherein said tube, said windows, and said stem are all made of alumina in order for said cell to be able to withstand temperatures of the highest order.

4. The optical cell of claim 1 wherein said tube, said windows, and said stem are all made of pyrex to provide economy at comparatively lower temperatures.

5. The optical cell of claim 1 wherein said tube, said windows, and said stem are made of lead glass, for economy when infrared light transmission through said cell is not required.

6. The optical cell of claim 1 wherein said windows are made of vitreous silica rod having an outside diameter just small enough to fit snugly inside the inside diameter of said cell body tube.

7. The optical cell of claim 1 wherein said windows are each of the order of five times as thick as the thickness of said cavity, for providing a cell capable of containig extremely high internal pressure of the order of 100 atmospheres, without outside support.

8. The optical cell of claim 1 wherein said radially extending hole is a drilled hole.

* * * * *